Dec. 21, 1954 F. C. CHANDLER Plant Pat. 1,331
ROSE VERBENA PLANT
Filed March 12, 1954
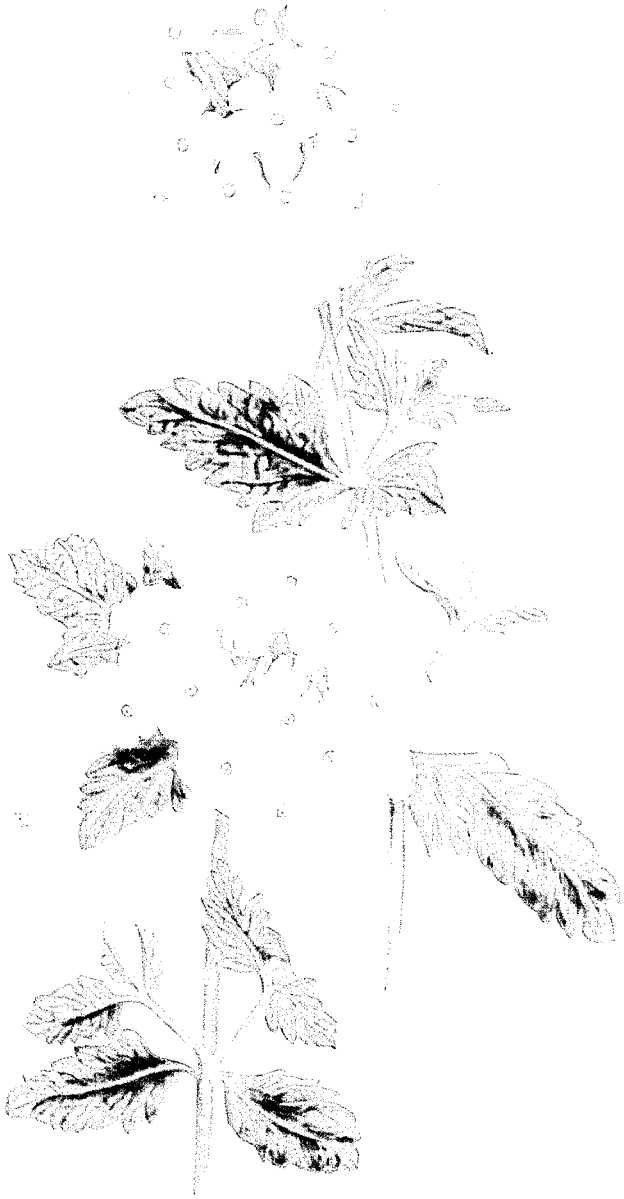
INVENTOR.
Florence Clyde Chandler
BY
Pennie, Edmonds, Morton, Barrows & Taylor
ATTORNEYS United States Patent Office Plant Pat. 1,331
Patented Dec. 21, 1954

1,331

ROSE VERBENA PLANT

Florence Clyde Chandler, Ardsley, N. Y., assignor to Boyce Thompson Institute for Plant Research, Inc., Yonkers, N. Y., a corporation of New York Application March 12, 1954, Serial No. 415,993

1 Claim. (Cl. 47—60)

This invention provides a new and distinct variety of rose verbena plant. The new variety of plant is particularly characterized by its unique rose-colored flowers which are exceptionally large forming large clusters of many flowers borne on long stiff stems, by its large dark green leaves, by erect habit, and by good vigor. The new variety has been reproduced asexually from cuttings and the characteristics appear to be fixed.

The distinct variety of rose verbena was produced by selecting a diploid seedling for its rose color from a bed of mixed verbenas and propagating it vegetatively. Cuttings from these actively growing plants were treated with colchicine. The branches which showed marked vigor were removed and propagated by cuttings. Chromosome studies show that this plant is a tetraploid with $2n=20$ chromosomes.

The new variety of plants as thus originated were asexually reproduced from cuttings at Boyce Thompson Institute for Plant Research, Inc., at Yonkers, New York.

In the accompanying drawing a plant of the invention is illustrated as a painting of a mature plant in substantially full bloom.

*Flowers*

The individual flowers are frequently over one inch in diameter and according to Ridgway the corolla is nearest Eugenia red with lighter areas toward the center of begonia rose. In young flowers the eye is greenish white. Munsell's color R*p*–R 5/10 (red purple red hue, 5 value, and 10 chroma) is nearest the flower color. There are generally from 28 to 38 flowers produced in a single cluster which is borne on an erect stiff stem around ⅛ inch in diameter and as much as 18 inches in length. These flower clusters are usually from 3 to 3½ inches in diameter and since the stems are erect the clusters are usually held around 13 inches above the ground. The vegetative vigor, increased flower size, and number of flowers per cluster distinguish this plant from the diploid with $2n=10$ chromosomes from which it was derived, as well as from other diploid verbenas.

*Seed*

No seed has been obtained from fully controlled self-pollinations, and the plants are reproduced only by means of vegetative cuttings. The pollen is about 67% aborted and the grains are from 57 to 87 microns in diameter.

*Leaves*

The leaves are thick and dark green and are generally around 3¼ inches long and around 2¼ inches in diameter near the base, while the leaves near the tips of the branches are smaller.

*General*

This new plant is much more vigorous and robust than the old variety of Spectrum Red verbena. To many people the plant has noticeable but slight fragrance. The plant remains in good vegetative condition throughout the summer and the leaves remain green and do not burn during the summer. The plant flowers well and has a profusion of bloom throughout the summer and until killed by frost.

I claim:

A new and distinct variety of rose verbena plant substantially as illustrated and described, characterized by very large individual flowers with the corolla nearly Eugenia red with lighter areas toward the center of begonia rose, in large clusters of many flowers, borne on stiff, erect and long stems, by large, thick and dark green leaves, and by good vigor.

No references cited.